United States Patent [19]

Schoendorfer et al.

[11] Patent Number: 4,816,151
[45] Date of Patent: Mar. 28, 1989

[54] ROTOR DRIVE FOR MEDICAL DISPOSABLES

[75] Inventors: Donald W. Schoendorfer, Santa Ana; Warren P. Williamson, IV, Huntington Beach, both of Calif.

[73] Assignee: Baxter International Inc., Deerfield, Ill.

[21] Appl. No.: 79,256

[22] Filed: Jul. 29, 1987

Related U.S. Application Data

[62] Division of Ser. No. 727,585, Apr. 26, 1985, Pat. No. 4,753,729.

[51] Int. Cl.⁴ ............................................ B01D 17/038
[52] U.S. Cl. .................................. 210/360.1; 210/541; 210/542
[58] Field of Search ................... 435/312, 311, 317; 210/360.1, 232, 541, 542, 433.2; 215/DIG. 8; 366/273, 274, 315, 316, 317; 416/3, 142, 143

[56] References Cited

U.S. PATENT DOCUMENTS

| 4,004,981 | 1/1977 | Hurni et al. | 435/312 |
| 4,162,855 | 7/1979 | Bender | 366/317 |

FOREIGN PATENT DOCUMENTS 0112152  6/1984  European Pat. Off. .
747682  4/1956  United Kingdom .

Primary Examiner—Frank Sever
Attorney, Agent, or Firm—Paul C. Flattery; Bradford R. L. Price; Gregory L. Roth

[57] ABSTRACT

A disposable biomedical rotating filtration system for processing fluids in a closed environment includes a rotor mounted for rotation on a pivot pin, a seal between the rotor and pivot pin, an external permanent magnet drive mechanism, and a star shaped drive element mounted on the rotor for rotating the rotor in response to a magnetic field induced by the permanent magnet of the drive mechanism. The drive element on the rotor is stamped from an inexpensive non-permanent ferromagnetic sheet metal and has a configuration and position in relation to the center of said magnetic field such that said drive element receives sufficient torque for driving said rotor and sufficient seal force is applied on the rotor to provide fluid tight seal between the rotating rotor and the seal. The pivot pin is molded from a hard plastic material such as a polyamide base resin having a low coefficient of friction and good lubriciousness. The pivot pin is irradiated by gamma radiation for sterilization and modifying of the plastic material without degradation or loss of lubricious properties.

26 Claims, 3 Drawing Sheets

ROTOR DRIVE FOR MEDICAL DISPOSABLES

CROSS REFERENCE TO RELATED APPLICATION

This application is a division of application Ser. No. 727,585, filed Apr. 26, 1985 and now U.S. Pat. No. 753,729.

BACKGROUND OF THE INVENTION

This invention relates to systems for fluids separation embodying a rotor within a housing and particularly to medical disposable units in which the rotor is retained by bearings and driven by an external magnetic drive. A particular area of usefulness of the present invention is hemapheresis, relating to the separation of one or more constituents of blood, using disposable filtration or centrifugal separation devices. A specific area of application is in a disposable plasmapheresis disposable device for the filtration of plasma from whole blood.

Plasmapheresis apparatus presently employed includes membrane filtration devices as exemplified by the device disclosed and claimed in application Ser. No. 591,925, filed Mar. 21, 1984 for "Method And Apparatus For Separation Of Matter From Suspension," by Donald W. Schoendorfer. Such membrane filtration device has an interior spinner which is covered with a filter membrane and includes a conduit system for collecting the plasma passing through the membrane. For plasmapheresis, such a filtration unit receives whole blood in the space between the spinner and the outer wall of the housing. The plasma in the blood filters through the membrane into corrugations on the surface of the spinner and then passes through radial holes into a central conduit. From the central conduit the plasma flows to the bottom of the spinner where it passes out through an outlet conduit in a pivot pin concentric with a central axis of the spinner device.

The spinner is mounted in a closed shell or housing and is driven remotely by magnetic intercoupling between a permanent magnet at the top of the spinner and an external rotating magnetic drive. The spinner is rotated at a high rate, such as 3600 RPM, to establish a precisely controlled enhanced vortex action which provides excellent plasma throughput rates without hemolysis. In the plasmapheresis application the disposable spinner is run, continuously or intermittently, for a period seldom greater than 40 minutes.

The upper end of the spinner is held in a pivot pin bearing during rotation and the lower end rests on the second, lower pivot pin bearing which has a central bore to permit downward passage of plasma filtrate to the outlet. An O-ring seal is generally positioned between the spinner and the lower pivot pin bearing to prevent mixture of whole blood or packed cells outside the spinner with plasma moving along the central axis.

In the plasmapheresis instrument presently employed there are four permanent magnets in the external drive mechanism. Such magnets are composed of samarium cobalt and are relatively powerful for permanent magnets. Barium ferrite magnetic elements, supplied in an unmagnetized state, are used for the rotor of the separator. After being magnetized with an impulse magnetizer, the resulting permanently magnetized elements are then cemented to the inside of a rotor cap which is then solvent bonded to the rotor. While this system is satisfactory in operative respects, it is relatively costly. It is essential that hemapheresis units of the type described above be manufactured as inexpensively as possible, because disposable units are used to prevent cross-contamination.

Moreover, the magnetic forces exerted by the permanent magnets are quite variable because the formulations of the raw magnetic materials are not precisely controllable. When the formulation varies, the magnetic field strength produced by the magnetization process varies, which in turn alters both the seal force and the torque available to rotate the rotor. Thus, the material of the permanent magnet and the magnetization process must be monitored very carefully to assure operation within narrow tolerances for operating consistency, and added cost factors are introduced.

The magnetic coupling between the magnetic structure on the rotor with the external permanent magnets on the drive mechanism must provide two functions. One is to generate sufficient torque to spin the rotor without slippage at high speed to provide superior filtration, while the other is to apply sufficient downward force to maintain the O-ring seal integrity without excessive wear.

SUMMARY OF THE INVENTION

A low cost, disposable fluid separating device includes an outer, generally cylindrical shell, a rotor disposed for rotation within the shell and a motor magnetically coupled to rotationally drive the rotor about a central axis of the shell and rotor. Upper and lower pivot pins support the rotor relative to the shell for rotation about the central axis. A nonmagnetized, high permeability magnetic coupling plate is affixed to the top of the rotor within a magnetic field generated by a set of permanent drive magnets which are arranged to be rotationally driven by the motor about the central axis.

Peripheral eccentricities in the coupling plate rotationally lock the plate to the drive magnets while a predetermined axial disposition between the coupling plate and drive magnets produces a precise downwardly directed axial force upon the coupling plate which remains constant during normal operation. Such force is transmitted downward from the coupling plate to the rotor to maintain a desired sealing pressure between the bottom of the rotor and the lower pivot pin which is sufficient to maintain a proper seal without being so great to produce unacceptable frictional heat or wear in the seal area.

A non-permanent ferromagnetic material of which the coupling plate on the rotor is composed is an inexpensive sheet metal which can be stamped or punched readily into a suitable configuration. A configuration in the form of a four-armed star provides adequate rotational torque and seal force within the desired range, when the sheet metal rotor drive is positioned a suitable distance above the center of the magnetic field induced by the permanent magnet of the exterior drive mechanism.

A superior drive and support mechanism for the rotor in rotary disposable biomedical devices utilizes a non-permanently magnetized ferromagnetic drive element on the rotor, in conjunction with molded plastic pivot pin bearings for the rotor, as described and claimed in the application entitled "Pivot Pin Bearing For Biomedical Systems," Ser. No. 722,707, filed Apr. 12, 1985, by W. Williamson and D. W. Schoendorfer. The pivot pin of the latter application is in the form of a molded plastic material having qualities of lubriciousness and hardness enabling it to withstand the stresses of supporting the rotor in high speed operation. The pivot pin is preferably constructed of particular plastic materials which are injection moldable. Such molded plastic pivot pins are gamma irradiated for sterilization and for modifying the pivot pin to provide a surface having a low coefficient of friction so as to permit operation of the rotor on the pivot pin for the required length of time to provide the desired liquid separations. A particularly effective pivot pin has been found to be formed of an injection molded polyamide based resin.

BRIEF DESCRIPTION OF THE DRAWINGS

A better understanding of the invention may be had by reference to the following description, taken in conjunction with the accompanying drawings, in which.

DETAILED DESCRIPTION OF THE INVENTION

Figure 1:
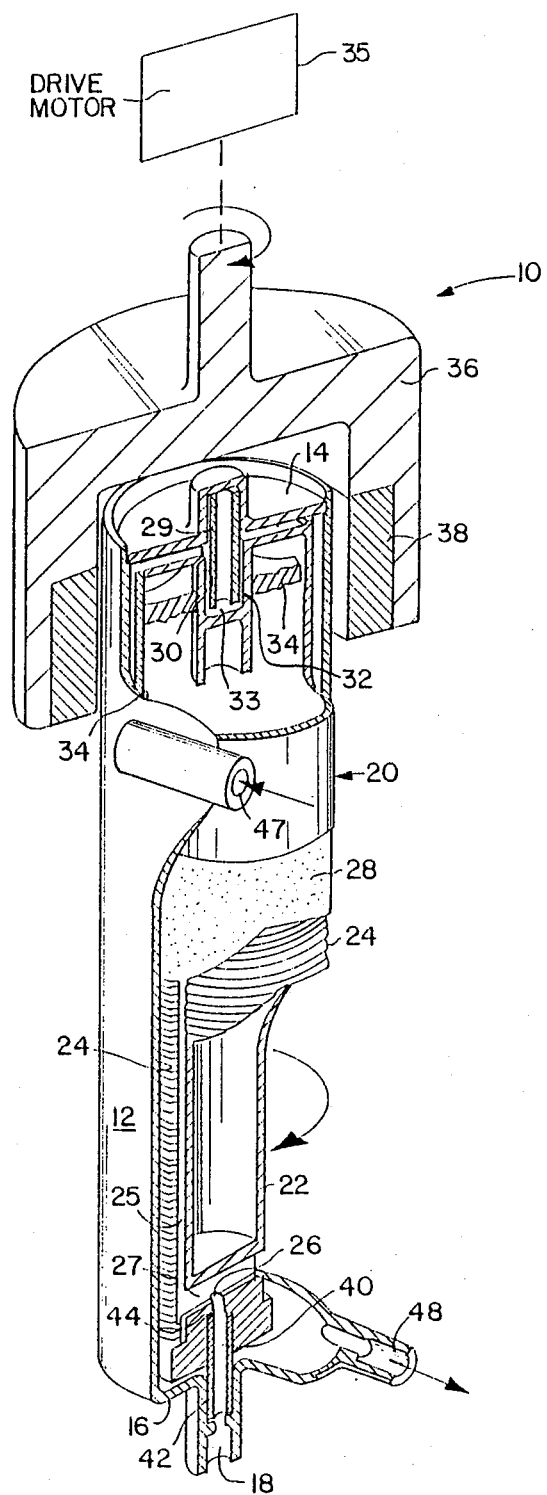
FIG. 1 is a perspective view, partly broken away, of a closed disposable unit embodying a ferromagnetic drive element on the rotor and molded plastic pivot pin, according to the invention.

Referring to FIG. 1, a disposable plasmapheresis device 10 is illustrated with which the non-ferromagnetic rotor drive and molded plastic pivot pin of the invention can be employed. The device comprises a cylindrical housing 12 completed by an upper end cap 14, the walls of which are non-magnetic, and a bottom end housing 16 terminating in a plasma outlet port 18 concentric with the central axis.

A spinner or rotor 20 is mounted in a vertical position between the upper end cap 14 and the opposed bottom end of housing 16. The spinner 20 comprises a shaped central mandrel 22, preferably of a light weight, strong, impermeable synthetic resin material such as high density polypropylene or ABS (acrylonitrile-butadiene-styrene resin). To simplify molding, the spinner may be made in two separate pieces (not shown) that are joined together. The outer surface of the central mandrel 22 is shaped to define a series of spaced apart circumferential grooves or plasma channels 24 in the outer periphery of the mandrel. The channels 24 are intersected by longitudinal grooves 25 parallel to the axis of rotation that communicate with a central axial bore 26 via radial conduits 27. The axial bore 26 is in line with and feeds plasma to the outlet port 18.

The surface of the rotary spinner 20 is covered by a cylindrical membrane 28 such as a commercially available filtration membrane of the type sold under the designation polyvinylidene fluoride by Millipore.

Figure 2:
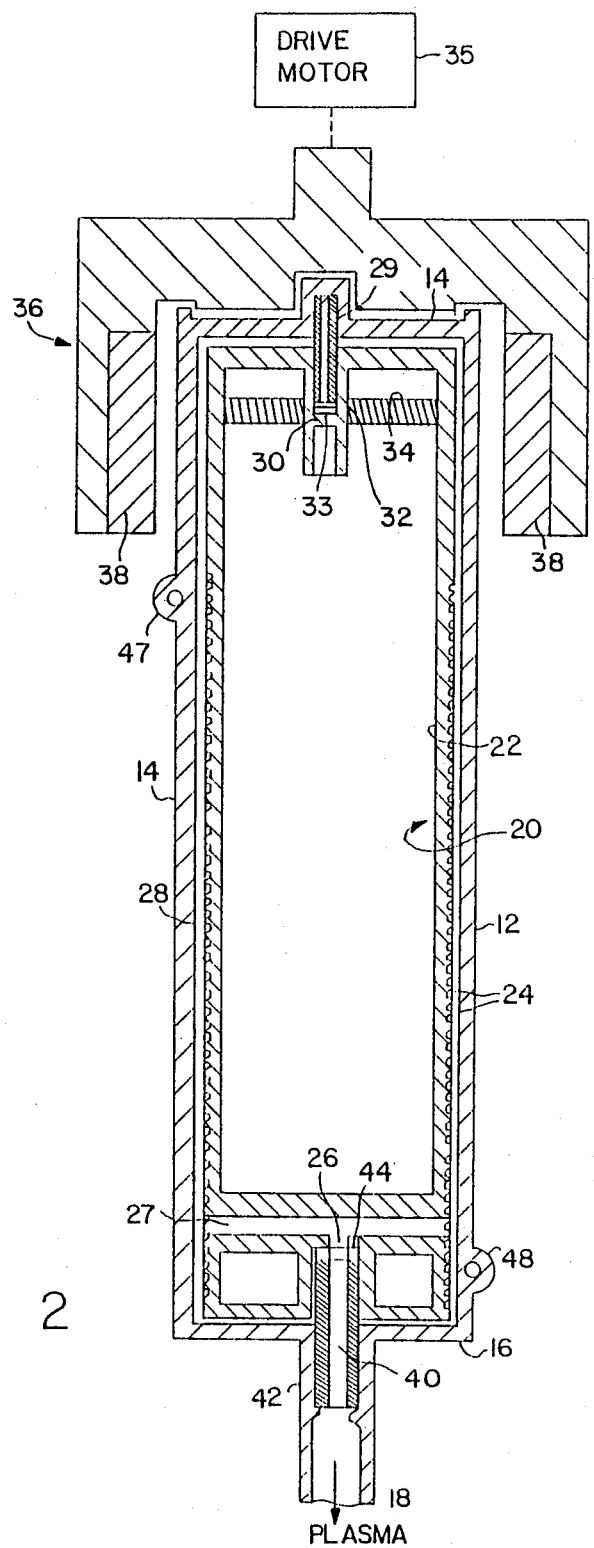
FIG. 2 is a cross sectional view of the structure of FIG. 1 mounted on the rotor above the center of the magnetic field produced by the permanent magnets of the exterior drive mechanism.

Referring particularly to FIG. 2, the rotary spinner 20 is mounted in the upper end cap 14 to rotate about an upper pivot pin 29 which is press fitted at its upper end in the end cap 14, the lower end of the pin being seated within a cylindrical bearing surface 30 in an end cylinder 32 attached to or forming an integral part of the rotary spinner 20. The lower end of the pin 29 protrudes into a small chamber 33 adjacent the bearing surface 30 so that the lower end of pin 29 does not dig into the end cylinder 32.

Mounted on the central axis of the end cylinder 32 as by ultrasonic striking is a ferromagnetic drive element 34 according to the invention, formed of sheet metal and having a configuration described in greater detail below. The element 34 is utilized in indirect driving of the spinner 20. For this purpose, a drive motor 35 exterior to the housing 12 is coupled to turn an annular drive member 36 which partially surrounds the non-magnetic end cap 14. The drive member 36 includes four samarium cobalt internal permanent magnets 38 which are equally spaced about an inner circumference of drive member 36. The magnets 38 provide a permanent magnetic field across the interior of the end cap 14 and induce magnetic fields through the ferromagnetic rotor drive element 34. Thus, as the annular drive member 36 is rotated, there is magnetic coupling between the ferromagnetic drive element 34 interior to the housing and the permanent magnets 38 exterior to the housing, locking the spinner 20 to the exterior drive, and causing the spinner to rotate without slippage. A rotational speed of the order of about 3600 RPM is used in this example, although higher rotational rates can be used.

Figure 3:
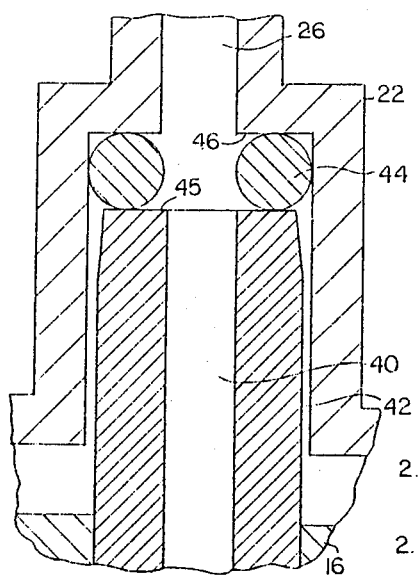
FIG. 3 is a sectional schematic detail of the lower portion of the rotor, the lower pivot pin and O-ring seal employed in the device of FIG. 1.

Referring particularly to FIG. 3, at the lower end of the rotary spinner 20, the central bore 26 communicates with a central aperture 40 in a cylindrical lower end pivot pin 42 concentric with the central axis and seated in the bottom end housing 16. An O-ring seal 44 is mounted on a bearing surface 45 at the upper end of the pivot pin 42. The upper end of pivot pin 42 has a conical taper with its smallest radius adjacent the surface 45 which prevents the edge of surface 45 from gouging the interior bearing surface of rotor 20 in the event of a relative wobble between pin 42 and rotor 20. An internal shoulder 46 at the lower end of the rotor 20 rests on the O-ring seal 44. The O-ring seal is fabricated preferably of a "Viton" material, manufactured by Du Pont and comprising one or more of a series of fluoroelastomers based on the copolymer of vinylidene fluoride and hexafluoropropylene and is specifically formulated for medical applications. The O-ring is covered with a silicone lubricant to reduce friction and wear. Thus, the rotor 20 and the O-ring 44 ride on top of the bearing surface 45 of pivot pin 42, and the rotor is supported at its center of rotation by the upper and lower pivot pins 29 and 42.

The pivot pin 42, according to the present invention, is molded from suitable organic polymers which confer certain important characteristics on the pivot pin as described in greater detail hereinafter. The upper pivot pin 29 is preferably in the form of a cylindrical plastic pivot pin molded of the same polymers as the lower pivot pin 42.

Referring again to FIG. 1, in operation, with the rotary spinner 20 rotating, for example at 3600 RPM, whole blood is fed through an input port 47 which directs the blood into a region or space between the spinner 20 and the outer wall of the housing 12. The plasma is filtered through the cylindrical membrane 28 into the interior of the spinner and passes downwardly through the plasma channel 27 and aperture 40 to be discharged through the outlet port 18. Packed blood cells with the plasma removed are discharged via an outlet port 48 at the bottom of the device.

A plasmapheresis device of the general type described above is described and claimed in detail in the above-identified copending Schoendorfer application. Except for the design and construction of the ferromagnetic rotor drive element and molded pivot pin bearings of the present invention, employed in conjunction with the plastic rotor and O-ring seal, the structure of the plasmapheresis device described above and in the above application, forms no part of the present invention.

The magnetic coupling of the ferromagnetic rotor drive element 34 to the permanent magnets 38 of the external drive mechanism 36 provides two different functions. The first is to generate sufficient torque to spin the rotor synchronously at the proper rotational rate, e.g. 3600 RPM, to separate whole blood into plasma and packed cells with enhanced vortex action. The second function is to generate sufficient downward seal force on the rotor against the O-ring to keep the O-ring 44 and the rotor 20 pressed against the pivot pin 42 so that red cells do not leak into the separated plasma flow in the central bore 40 of the lower pivot pin 42. There are two components of downward force on the rotor. The first is the weight of the rotor and the second is a downward force generated by the interaction of the ferromagnetic rotor drive element 34 of the rotor with the external permanent magnets 38 in the external magnetic drive mechanism 36. In the specific plasmapheresis device of the present invention these two forces should add up to between 370 and 450 grams of total force. Sufficient torque for spinning the rotor at the above noted speed is generated even though the ferromagnetic rotor drive element 34 is constructed of inexpensive sheet metal of a suitable configuration by a simple stamping or punching process.

Figure 4:
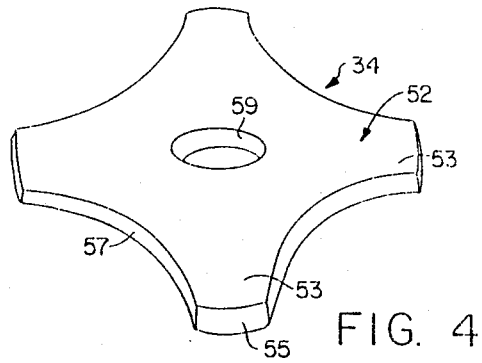
FIG. 4 illustrates a particular ferromagnetic rotor drive element in the form of a star-shaped sheet metal piece having four truncated arms.

Referring now to FIG. 4, the rotor drive element 34 is made in the form of a stamped sheet metal star 52 having four arms 53 with truncated ends 55 and concave profiles 57 defining the sides of the arms 53. This configuration provides the equivalent of magnetic pole tips in the arms 53, but also includes substantial material in an annulus about the center aperture 59. Both circumferential and downward forces are thereby exerted, and at adequate levels, by the exterior magnetic drive.

The rotor drive element 34 having the star shaped configuration 52 shown in FIG. 4 can be produced e.g. from 8 gauge sheet metal stock (0.164±0.008") hot rolled sheet. The metal stock is sheared into working size and passed through a belt sanding unit to remove any scale left on the surface by the mill rolling process. The material is then punched into the modified star shape 52 on a high speed turret press. The resulting part or slug 52 is then vibratory deburred to remove the sharp edges incurred by punching. The resulting part is then electroplated with a thin nickel coating to prevent corrosion. The thickness of the element 52 can range from about 0.156 to about 0.172 inch. The cost of the resulting star shaped rotor drive element 52 is less than one-tenth that of the permanent magnet rotor drive heretofore employed. It has been experimentally determined that the limiting factor with respect to the torque transmitted to the rotor with the previously employed permanent magnet on the rotor is the power overload circuitry to the drive motor on the external driving mechanism. Thus, if one increases resistance to rotation of the rotor, eventually the drive motor draws enough current to trip the circuit breaker. This occurs before there is slippage between the permanent magnet field of the samarium cobalt magnets of the external drive, and the permanent magnet in the rotor. It has also been determined by testing the presently employed plasmapheresis unit that the necessary downward seal force must be between 370 and 450 grams. Less seal force induces leakage of red cells into the plasma and more seal force induces premature failure of the seal due to wear.

Figure 5:
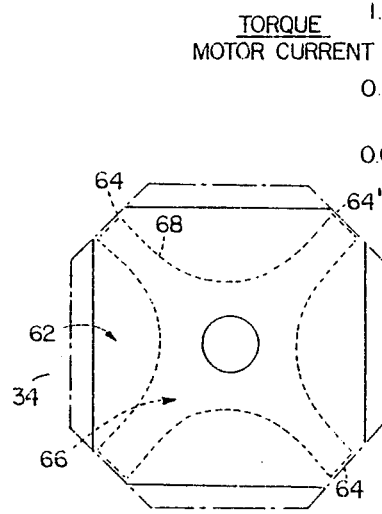
FIG. 5 is a plan view of a second configuration of ferromagnetic rotor drive element which induces both adequate torque and downward seal force, and includes dotted and dot-dash outlines of other configurations.

FIG. 5 depicts a ferromagnetic member 34 in the form of a substantially square element 62 having diagonals 64 at the corner tips, which accentuate downward seal force. Torque is reduced from the design of FIG. 5, because of the more uniform radial dimension of the element 62, but this configuration is useful where lower torque and more downward force are needed. It will be understood that nominal axial displacement of the element 34 can be below the center of the drive magnets to reduce total force on the seal, where this is appropriate. For greater downward force at some further expense in torque, a larger area element 64' having larger excised corners can be used, as shown by the dot-dash lines.

In FIG. 5 there is also shown, in dotted lines, the outline in plan of a modified star-shape 66 in which the arms 68 are relatively narrow and well separated. In this configuration torque is maximized with a reduced but still acceptable level of downward force on the O-ring seal.

Figure 6:
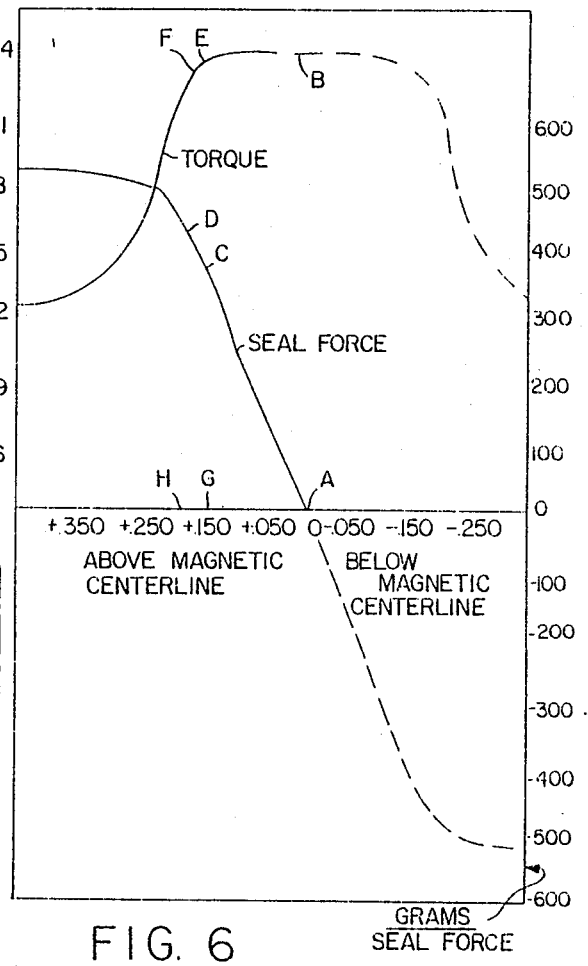
FIG. 6 is a graph illustrating torque and seal force for the rotor drive element of FIG. 4 in a plasmapheresis device, as a function of vertical displacement of the ferromagnetic drive element as shown in FIG. 2.

FIG. 6 is a chart showing the relation between the seal force and the torque as the ferromagnetic drive element 34 is varied in its vertical position relative to the permanent magnets 38 of the external drive mechanism 36. Torque values shown in the chart are units of current required to break the synchronous coupling between the samarium cobalt magnets 38 and the ferromagnetic element 34. These units do not correlate to any standard of measure but give relative readings when compared to the current necessary for the separation of blood. Seal force on the chart is directly read in grams. A special tool was employed to measure the seal force at the precise dimension in which the rotor 20 lifts of the pivot pin 42 and seal 44.

In FIG. 6, it is seen that if the ferromagnetic drive element 34 is mounted in the direct center of the magnetic field generated by the external magnetic drive system, shown at point A in FIG. 6, a zero seal force is obtained together with the highest torque value, as indicated by point B. Moving the sheet metal drive element 34 below the center of the magnetic field generated by the external drive system, (i.e. moving to the right of point A in FIG. 6) generates a negative seal force, as the interaction of the magnetic field with the ferromagnetic drive element 34 tends to elevate the rotor. On the other hand, moving the drive element 34 above the center point A of the magnetic field produces a positive seal force as the interaction of the magnetic field with the ferromagnetic drive element 34 tends to push the rotor downward. Therefore, for proper operation the sheet metal drive element 34 should be above the center of the magnetic field generated by the external permanent magnets 38.

As shown in FIG. 6, translation of the rotor drive element 34 away from the center point A in either direction diminishes the torque that the rotor will receive. The objective is to tune the rotor drive element configurations of FIGS. 4 and 5, particularly an element such as the star shape 52 of FIG. 4, and to place such rotor drive element a proper distance above the center point A of the magnetic field so as to have available the maximum torque to drive the rotor for the separation of blood, and to have sufficient seal force, preferably 370 to 450 grams of seal force, to prevent leakage of red cells past the O-ring seal 44 into the separated plasma in the central bore 40 of the lower pivot pin 42. This tuning is done with an additional constraint of minimizing the cost of element 52 by minimizing the use of material and the manufacturing effort. Thus, for the rotor drive configuration 52 of FIG. 4, as shown in FIG. 6, in order to obtain a seal force of between 370 and 450 grams, indicated at points C and D, and maximum corresponding torque indicated at points E and F, the rotor drive element 52 should be positioned a vertical distance of between 0.150 and 0.20 inch above the center A of the magnetic field, as indicated by points G and H in FIG. 6.

The plastic pivot pin indicated at 42 in FIG. 3 is a molded pivot pin of a hard plastic material having a low coefficient of friction and having lubriciousness and wear resistance, so that the rotor spinning against the plastic pin does not create hot spots on the pin or shed debris. Another important consideration is that the entire device is irradiated by gamma radiation, as by a cobalt 60 source, not only for sterilization purposes, but for additional modifying of the plastic pivot pins, without degradation or loss of the lubricious properties of the pivot pins. Another criterion is that it is necessary to conform to the FDA toxicity requirements for blood compatability and donor safety. There has been significant work accomplished in the field of polymer science in development of inherently lubricated polymers for wear applications, including the use of base polymer with various additives, including, for example, polytetrafluoroethylene, silicone, glass fiber and carbon fiber.

It was found that plastic pivot pins having the above noted required properties for use in biomedical applications could be economically produced by injection molding of suitable polymer materials, preferably Nylon 6/6 based RL 4730, a polyamide based polymer modified with PTFE and Silicone oil. These injection molded polyamide based pivot bearings, such as at 42 of FIG. 3, were found least susceptible to wear when employed in the plasmapheresis device described above, in conjunction with the ferromagnetic rotor drive element described above. Other polymers capable of being injection molded, and after irradiation in the manner described above, also provided suitable results. These polymers included Polyetherimide and Nylon 12. The cost of such injection molded plastic pivot pin bearings is substantially below the cost of the stainless steel pivot pin bearings heretofore employed in the prior art.

From the foregoing, it is seen that the invention provides a novel inexpensive ferromagnetic rotor drive element replacing the prior art permanent magnet rotor drive, and which is highly advantageous and applicable particularly for use in biomedical applications where it is necessary to separate fluids, as by filtration, e.g. in hemapheresis, in a closed environment employing a seal, and where the device is disposable. The ferromagnetic rotor drive element of the present invention is particularly effective in combination with a molded plastic pivot pin bearing used in conjunction with an O-ring seal, such as to permit operation of the separation unit for a sufficient period under the conditions of force which have to be exerted, to collect the required amount of product, e.g. units of plasma, after which the device is discarded, and results in substantially reduced cost of the device.

Since various changes and modifications of the invention will occur to and can be made readily by those skilled in the art without departing from the invention concept, the invention is not to be taken as limited except by the scope of the appended claims.

What is claimed is:

1. In a disposable biomedical system for processing fluids in a nonrotating housing providing a closed environment comprising a rotor mounted for rotation within the housing, a seal between rotating and nonrotating portions of the biomedical system having fluid communication therebetween, an external magnet drive mechanism, and a drive element mounted on the rotor for rotating the rotor in response to the magnetic field wherein the drive element on the rotor is of a non-permanent ferromagnetic material having a non-circular perimeter configuration and position in relation to the center of said magnetic field such that said drive element receives sufficient torque for driving said rotor and sufficient downward seal force is applied on the rotor by the magnetic field to provide fluid sealing between the rotating and nonrotating portions of the biomedical system.

2. The system of claim 1, wherein the drive element mounted on the rotor is positioned above the center of said magnetic field to apply a downward force on the rotor.

3. The system of claim 2, wherein the drive element mounted on the rotor is composed of sheet metal.

4. The system of claim 3, wherein the drive element mounted on the rotor is in the form of a square.

5. The system of claim 4, wherein the square has rounded corners.

6. The system of claim 3, wherein the drive element mounted on the rotor is in the form of a cross, the four arms of which are of equal length.

7. The system of claim 3, wherein the drive element mounted on the rotor is star shaped and has four corners, and wherein the star has four sides each having an arcuate concave outer surface.

8. The system of claim 2, wherein the drive element mounted on the rotor is stamped out of a sheet of metal.

9. A disposable biomedical system for processing fluid in a closed environment comprising:
   a plastic rotor mounted for rotation about a central axis on a molded pivot pin of a hard plastic material having a low coefficient of friction and lubriciousness, and which is capable of being irradiated by gamma radiation for sterilization of the plastic material without degradation or loss of lubricious properties said rotor and pivot pin having fluid communication therebetween;
   a seal between the rotor and pivot pin;
   an external magnetic drive mechanism producing a magnetic field which rotates about the central axis; and
   a drive element mounted on the rotor for rotating the rotor in response to the magnetic field produced by the drive mechanism, said drive element being of a non-permanent magnetic material having a non-circular perimeter configuration and a position in relation to the center of said magnetic field such that said drive element receives sufficient torque for driving said rotor and sufficient seal force is applied through the drive element to the rotor by the magnetic field to provide fluid sealing between the rotating rotor and the seal.

10. The system of claim 9, wherein the seal is a silicone lubricated "O" ring, and the pivot pin is substantially cylindrical and hollow to permit passage of liquid, and the magnetic drive mechanism includes a plurality of permanent magnets producing the magnetic field.

11. The system of claim 10 wherein the pivot pin is tapered at the top adjacent to the seal.

12. The system of claim 11, said pivot pin being formed of an injection molded polyamide based resin.

13. The system of claim 12, wherein the drive element mounted on the rotor is star shaped and is composed of sheet metal, and is positioned above the center of said magnetic field.

14. In a disposable biomedical system for processing fluids in a closed environment comprising a rotor mounted for rotation, a pivot pin, a seal disposed at one end of the pivot pin between two surfaces having rotation relative to one another with one of the surfaces being on the pivot pin, an external magnet drive mechanism, and a drive element mounted on the rotor for rotating the rotor in response to a magnetic field induced by the drive mechanism; the improvement wherein the drive element on the rotor is of a non-permanent ferromagnetic material having a non-circular perimeter configuration and position in relation to the center of said magnetic field such that said drive element receives sufficient torque for driving said rotor and sufficient downward seal force is applied on the rotor by the magnetic field to provide fluid sealing between the seal and the two surfaces for providing fluid communication between the two surfaces.

15. The system of claim 14, wherein the drive element mounted on the rotor is positioned above the center of said magnetic field to apply a downward force on the rotor.

16. The system of claim 15, wherein the drive element mounted on the rotor is composed of sheet metal.

17. The system of claim 16, wherein the drive element mounted on the rotor is in the form of a square.

18. The system of claim 17, wherein the square has rounded corners.

19. The system of claim 16, wherein the drive element mounted on the rotor is in the form of a cross, the four arms of which are of equal length.

20. The system of claim 16, wherein the drive element mounted on the rotor is star shaped, and having four corners, and wherein the star has four sides each having an arcuate concave outer surface.

21. The system of claim 15, wherein the drive element mounted on the rotor is stamped out of a sheet of metal.

22. A disposable biomedical system for processing fluid in a closed environment comprising:
a plastic rotor mounted for rotation about a central axis;
a molded pivot pin of a hard plastic material having a low coefficient of friction and lubriciousness and a flat sealing surface at one end, and which is capable of being irradiated by gamma radiation for sterilization of the plastic material without degradation of loss of lubricious properties, said rotor and pivot pin having fluid communication therebetween;
a seal disposed between the flat sealing surface of the pin and a second flat sealing surface having a relative rotation with respect to the flat sealing surface of the pivot pin;
an external magnetic drive mechanism producing a magnetic field which rotates about the central axis; and
a drive element mounted on the rotor for rotating the rotor in response to the magnetic field produced by the drive mechanism, said drive element being of a non-permanent magnetic material having a non-circular perimeter configuration and a position in relation to the center of said magnetic field such that said drive element receives sufficient torque for driving said rotor and sufficient seal force is applied through the drive element to the rotor by the magnetic field to provide fluid sealing between the seal and each of said sealing surfaces.

23. The system of claim 22, wherein the seal is a silicone lubricated "O" ring, and the pivot pin is substantially cylindrical and hollow to permit passage of liquid, and the magnetic drive mechanism includes a plurality of permanent magnets producing the magnetic field.

24. The system of claim 23, wherein the pivot pin is tapered at the top and the top is adjacent to the seal.

25. The system of claim 24, whrein said pivot pin is formed of an injection molded polyamide based resin.

26. The system of claim 25, wherein the drive element mounted on the rotor is star shaped and is composed of sheet metal, and is positioned above the center of said magnetic field.

* * * * *